United States Patent [19]

Black et al.

[11] Patent Number: 5,031,443
[45] Date of Patent: Jul. 16, 1991

[54] APPARATUS FOR MEASURING BEARING TORQUE

[75] Inventors: John M. Black, Farmington; Athanasios Dellas, Bristol, both of Conn.

[73] Assignee: United Technologies Corporation, Hartford, Conn.

[21] Appl. No.: 485,662

[22] Filed: Feb. 27, 1990

[51] Int. Cl.⁵ ............................................. G01N 19/02
[52] U.S. Cl. ............................................................. 73/9
[58] Field of Search ............................................... 73/9

[56] References Cited

U.S. PATENT DOCUMENTS

| | | | |
|---|---|---|---|
| 3,127,761 | 4/1964 | Gordon | 73/9 |
| 3,178,928 | 4/1965 | Howe | 73/9 |
| 3,552,198 | 1/1971 | Friedland | 73/9 |
| 4,672,838 | 6/1987 | Reh | 73/9 |

Primary Examiner—Robert Raevis
Attorney, Agent, or Firm—Richard H. Kosakowski

[57] ABSTRACT

An apparatus measures torque in high accuracy, close tolerance, precision output axis suspension bearings and corresponding pivots. The bearings are received in corresponding apertures at the ends of axial aligned, rotatable test shafts. A pendulum, having an eccentric cylindrical shaped aperture for holding a pair of pivots in axial alignment, is disposed between the test shafts, the pivots being received in the bearings. The pendulum is further provided with a reflective panel; a laser light source is arranged to direct a beam of laser light onto the pendulum reflective panel, and a photosensitive position sensing array is oriented to sense a laser light beam reflected off the panel. The test shafts are rotated, and the magnitude of a deflection of the reflected laser light beam is measured by the array, and is directly proportional to torque in the bearings.

7 Claims, 3 Drawing Sheets

APPARATUS FOR MEASURING BEARING TORQUE

DESCRIPTION

1. Technical Field

This invention relates generally to bearing torque measurement and more particularly to apparatus for measuring torque in high-accuracy, close tolerance, precision gyroscope output axis suspension bearings.

2. Background Art

Advanced generation gyroscopes, such as the Hamilton Standard Model RI-1010 single degree of freedom, floated, rate-integrated gyroscope, require parts having greater accuracy and closer tolerance than previous generation gyroscopes. In particular, output axis suspension bearings and the associated pivots employed in such advanced generation gyroscopes require diametral clearances on the order of $1 \times 10^{-5}$ inches, as opposed to diametral clearances of about $2 \times 10^{-4}$ inches in previous generation gyroscopes.

Gyroscope component parts, such as suspension bearings and pivots, can be measured with an accuracy of within about 10 microinches using known measuring techniques. However, measurement accuracy of within 1 microinch is required to determine the acceptability of these component parts in advanced generation gyroscopes.

Because current measuring techniques do not allow sufficient accuracy to determine the acceptability of high accuracy gyroscope suspension bearings and pivots, these parts are currently tested by completely assembling a gyroscope, and then operating the gyroscope to determine if the torque developed in the bearings is within an acceptable level. However, this operational testing is very expensive because of the large expense and amount of time required in assembling advanced generation gyroscopes, and the high rate of untested suspension bearing and pivot pairs that produce unacceptable torque levels during operation.

DISCLOSURE OF INVENTION

Objects of the present invention include provision of improved torque measurement of high-accuracy, close tolerance, precision output axis suspension bearings and corresponding pivots which accurately predicts the acceptability of these bearings and pivots for use in precision gyroscopes.

According to the present invention, a bearing housing of each bearing in a pair of bearings is securely fixed to one end of a corresponding shaft in a pair of rotatable shafts, and the shafts and bearings are axially aligned; a pivot associated with each bearing is securely fixed on opposing sides of a pendulum, the pivots being eccentric to the pendulum center of gravity; the pivots are received in, and supported by, the ball bearings of each bearing for supporting the pendulum; driving means rotate the shaft pair, thereby rotating the bearings, and the angular displacement of the pendulum is measured, the angular displacement being proportional to torque developed in the bearings during rotation.

According further to the invention, reflecting means are secured to the pendulum, and a photosensitive array detects movement of a laser beam reflected from the reflecting means, the movement of the reflected laser beam being proportional to the angular displacement of the pendulum, and therefore being proportional to torque in the bearings.

The present invention represents an improvement over previous methods of testing high accuracy gyroscope bearings and pivots because a reliable qualitative analysis of the bearings and pivots can be rapidly performed at a reduced cost. Additionally, analysis of the test data, such as frequency analysis, allows a determination of the specific nature of any bearing defects, i.e., a geometric or material defect of a pivot or ball bearing, or contamination within the bearing. The bearings and pivots are pre-screened prior to installation in a gyroscope unit, thereby greatly reducing the rejection rate of completely assembled gyroscopes.

The foregoing and other objects, features and advantages of the present invention will become more apparent in light of the following detailed description of an exemplary embodiment thereof, as illustrated in the accompanying drawings.

BEST MODE FOR CARRYING OUT THE INVENTION

Figure 1:
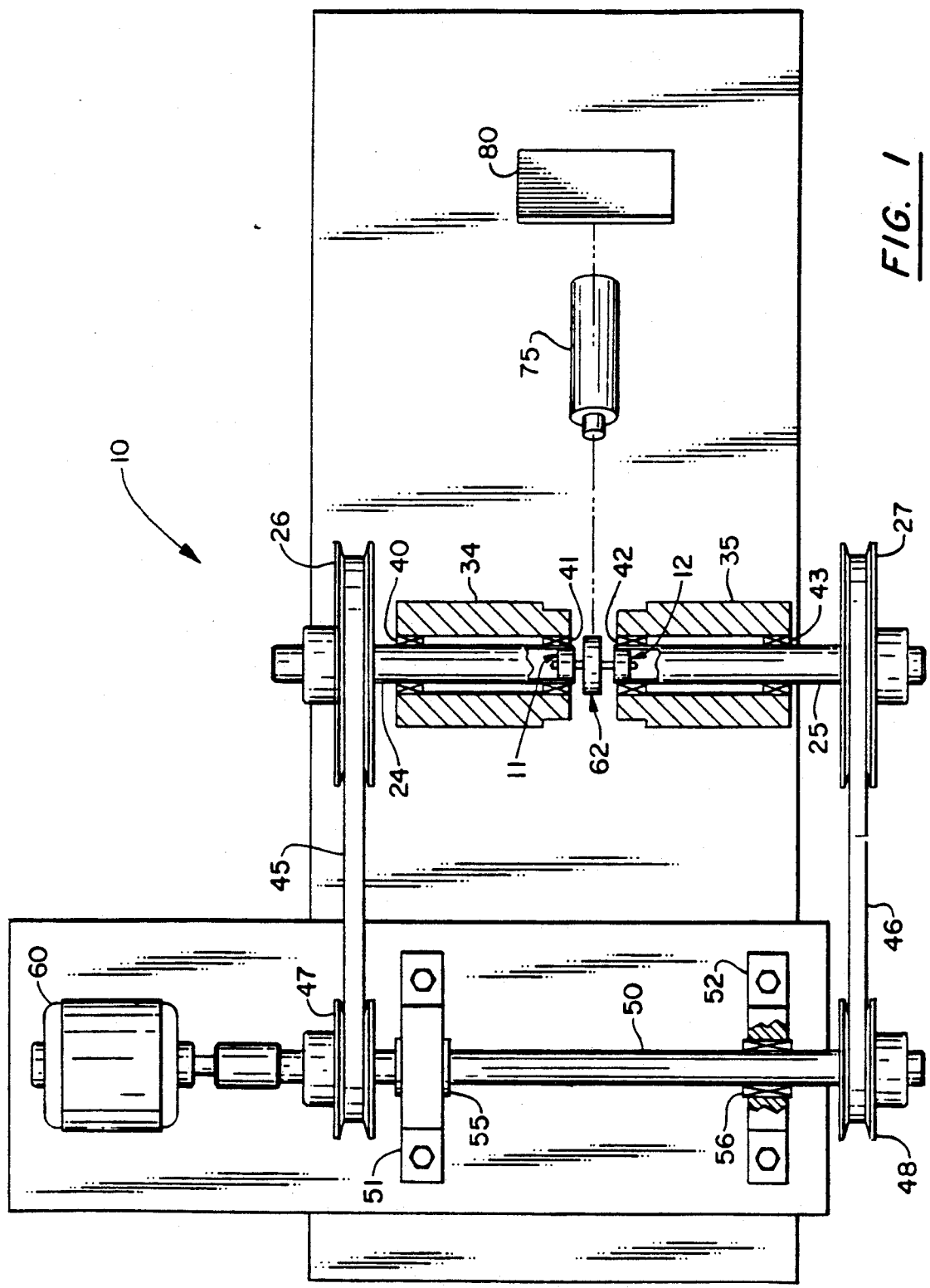
FIG. 1 is a top view, partially cut away, of apparatus for measuring torque in a pair of bearings.
Figure 2:
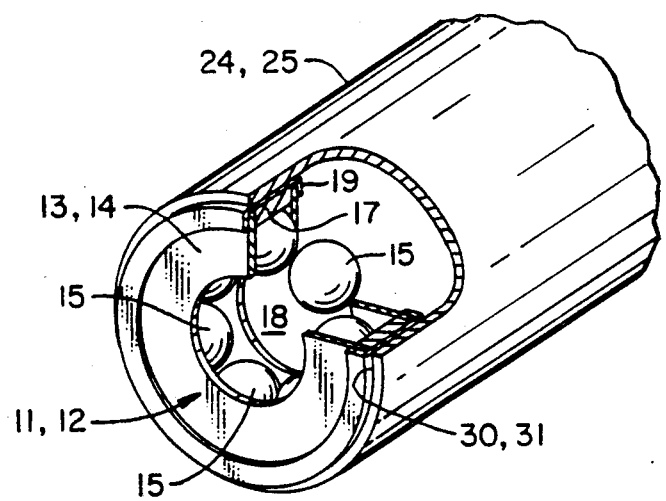
FIG. 2 is a perspective view, partially cut away, of a test shaft of the apparatus of FIG. 1, a bearing being received in a shaft aperture.

Referring to FIG. 1, an apparatus 10 for measuring torque in a pair of bearings 11, 12 is illustrated. The bearings to be tested may be precision bearings of the type illustrated in FIG. 2, and used in high accuracy, precision gyroscopes, e.g., a Hamilton Standard Model RI-1010 single degree of freedom, floated, rate-integrated gyroscope. More particularly, FIG. 2 illustrates a full compliment bearing 11, 12 having sapphire end plates 13, 14. Each bearing comprises a set of ball bearings 15 confined within a cylindrical outer race 17. The diameter of the outer race is selected to hold the ball bearings in a concentric circular formation, thereby forming a cylindrical aperture 18 in the center of the bearing concentric to the outer race 17.

Figure 3:
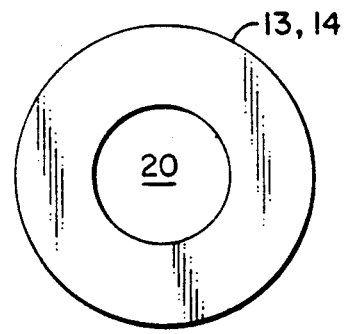
FIG. 3 is a side view of a bearing end plate of the bearing of FIG. 2.

Referring to FIGS. 2 and 3, the ball bearings 15 are retained in the outer race by the pair of end plates 13, 14. The end plates comprise a thin, resilient layer of retaining material, such as sapphire, held in relation to the outer race by a bearing housing 19. The end plates are circular in shape having a diameter equal to the diameter of the outer race, and also having a concentric circular aperture 20 slightly larger in diameter than the aperture 18 created by the ball bearings in the center of the bearings.

Referring to FIG. 2, each bearing housing 19 is cylindrical in shape and in concentric relation to the bearing outer race 17. The inside diameter of each housing 19 is slightly larger than the outside diameter of the corresponding outer race 17 so that the friction therebetween is sufficient to prevent relative motion between the outer race 17 and the housing 19.

The present invention is particularly well suited for supporting the aforedescribed bearing pair in axial alignment, thereby allowing the bearings to be tested with a pendulum of the present invention. Referring more particularly to FIGS. 1 and 2, each bearing 11,12 is supported at one end of a rotatable test shaft 24,25, the other end of each test shaft having a test shaft pulley 26,27. Each bearing 11,12 is received in a corresponding aperture 30, 31 at the end of each test shaft 24,25, the inside diameter of the aperture being slightly larger than the outside diameter of the bearing housing so that the housing can be press-fit snugly in the aperture with sufficient friction existing between the housing 19 and aperture 30,31 to prevent relative movement between the housing and the test shaft 24,25.

Each test shaft is supported in a test shaft housing 34,35 by a pair of support bearings 40,41,42,43, one support bearing in each pair located at either end of the test shaft housings. The support bearings may be of any known type capable of supporting a shaft for allowing ease of bidirectional rotation.

The shaft pulleys 26,27 are resiliently fixed to the shafts 24,25 for rotating the test shafts in the support bearings in response to rotating the test shaft pulleys 26,27. The test shaft pulleys are driven by a pair of drive belts 45,46, which are in turn driven by a pair of drive pulleys 47,48 mounted on a drive shaft 50. The drive shaft is supported in a pair of support brackets 51,52, by a support bearing 55,56 in each bracket. The drive shaft 50 is coupled to an electric motor 60, so that when the motor is operated, the drive shaft 50 and drive pulleys 47, 48 are rotated, and the drive belts 45, 46 are driven to drive the shaft pulleys 26,27 and rotate the test shafts 24,25. The motor, drive pulleys and test shaft pulleys are selected to rotate the test shafts at approximately 0.5 revolutions per minute in either direction to simulate actual gyroscope conditions.

Figure 4:
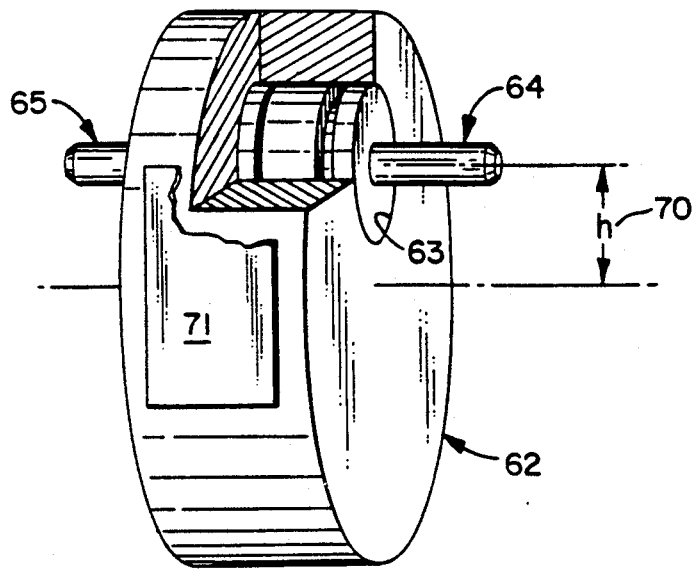
FIG. 4 is a perspective view, partially cut away, of a pendulum of the apparatus of FIG. 1 in relation to a pair of gyroscope pivots.
Figure 5:
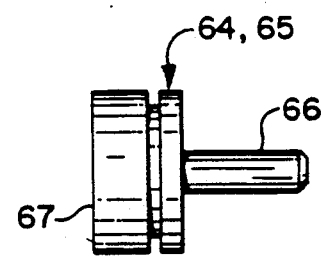
FIG. 5 is a side view of a gyroscope pivot of FIG. 4.

Referring now to FIG. 4, the pendulum 62 of the present invention is cylindrical in shape, having an eccentric cylindrical shaped aperture 63 for receiving a pair of gyroscope pivots 64,65. The pivots 64,65 are illustrated in FIG. 5 as having a cylindrical pivot shaft 66 resiliently fixed to a cylindrical pivot housing 67, the pivot housing 67 being of larger diameter than the pivot shaft 66.

Referring again to FIG. 4, the inside diameter of the pendulum aperture is slightly larger than the outside diameter of the pivot housing 67 so that the pivots 64,65 can be press fit into the aperture 63 on opposing sides of the pendulum, and the friction therebetween is sufficient to prevent relative movement between the pivots and the pendulum.

The pendulum is provided with a preselected mass (M) and eccentricity (h) 70, i.e., the distance between the axis of the pivots 64,65 and the pendulum center of gravity, so that the torque ($\tau$) required to rotate the pendulum 62 is given by the following relationship:

$$\tau = (M)(g)(h) \sin \Phi \quad \text{(eq. 1)}$$

where: g is the force of gravity; and $\Phi$ is the angular rotation of the pendulum.

Figure 6:
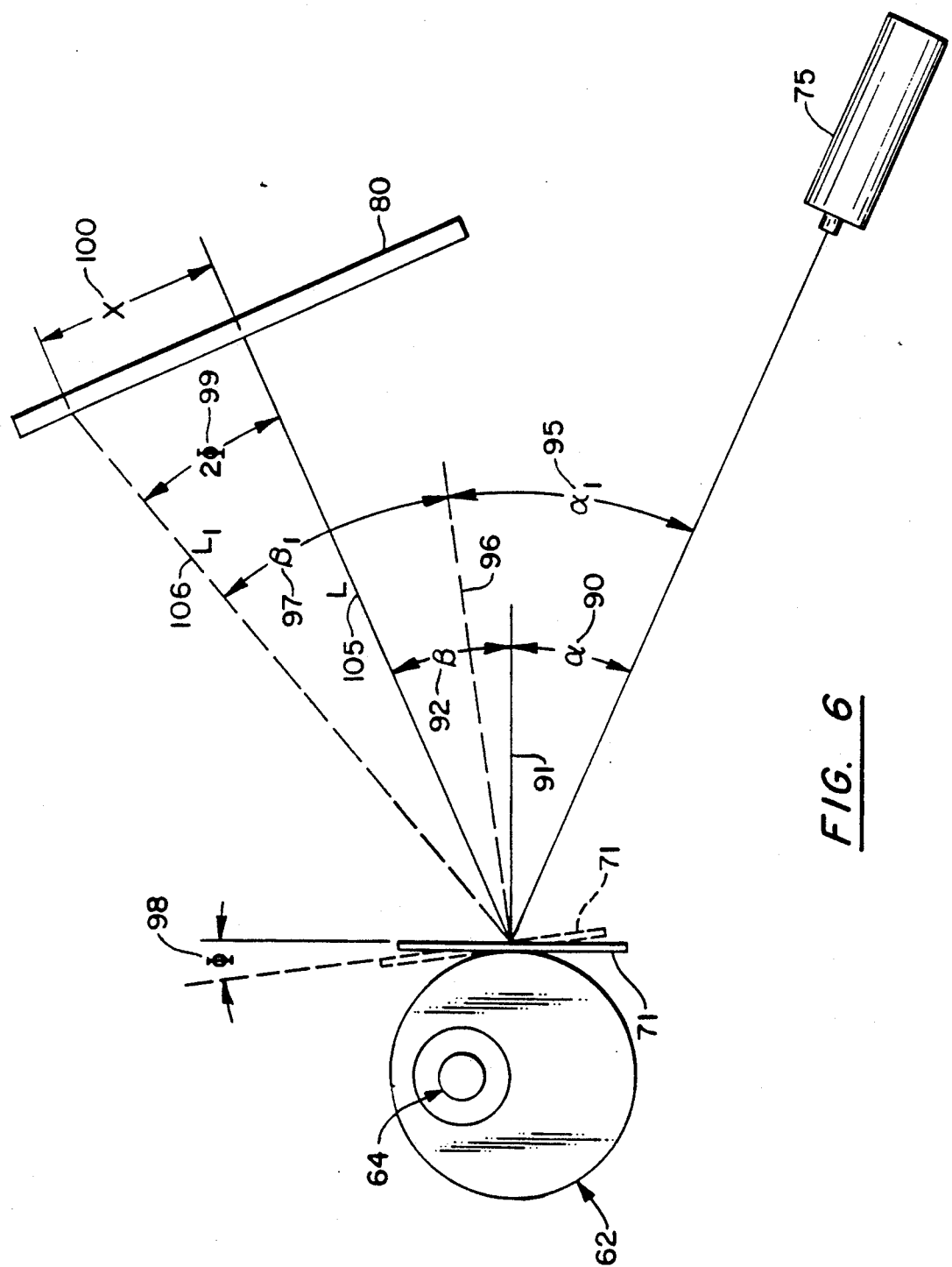
FIG. 6 is a schematic view of the apparatus of FIG. 1 showing the vertical relationship between a beam of laser light reflected off a pendulum reflective panel with the pendulum in a righted position, and with the pendulum in a displaced position.

The pendulum 62 is further provided with a reflective panel 71 made of coated glass or other reflective material. Referring to FIGS. 1 and 6, a laser light source 75, such as a He-Ne gas laser, is arranged to direct a beam of laser light onto the pendulum reflective panel 71. A photosensitive position sensing array 80 (array) is oriented so that a reflected laser light beam is sensed by the array 80.

FIG. 6 illustrates the relative position of the laser 75 and the array 80 in a plane perpendicular to the axis of the pendulum 65, and shows that the laser 75 and the array 80 are vertically displaced. The vertical reflection of the beam may be predicted by the following relationship derived from Snell's law:

$$\beta = \alpha \quad \text{(eq. 2)}$$

where: $\alpha$ 90 is the angle of incidence of the laser light with respect to an axis 91 perpendicular to the reflective panel; and $\beta$ 92 is the angle of reflection of the laser light with respect to the same axis 91.

If the pendulum 62 is rotated, the angle of incidence, $\alpha$ 90, is changed to a new angle $\alpha_1$ 95 with respect to an axis 96 perpendicular to the reflective panel, due to the displacement of the reflective panel, thereby producing a new angle of reflection, $\beta_1$ 97, equal to $\alpha_1$ 95. The change in the angle of incidence and reflection is directly related to the angular rotation of the pendulum ($\Phi$) 98, as given by the following relationship:

$$\alpha_1 - \alpha = \beta_1 - \beta = \Phi \quad \text{(eq. 3)}$$

The change in the angle of incidence and the angle of reflection of the laser beam produces a deflection (x) 100 of the laser beam on the array. The magnitude of the deflection is measured by the array, and is directly related to the change in the angle of incidence and angle of reflection of the laser beam (2$\Phi$) 99, and is therefore directly related to the angular rotation 98 of the pendulum. The angular rotation 98 of the pendulum is given by the following relationship:

$$\Phi = \tfrac{1}{2} \cos^{-1}\{((L^2 + L_1^2 - x^2) \div (2)(L)(L_1)\} \quad \text{(eq. 4)}$$

where: L 105 is the distance between the reflective panel 71 and the array 80 of a beam reflected at angle $\beta$ 92; and $L_1$ 106 is the distance between the reflective panel 71 and the array 80 of a beam reflected at angle $\beta_1$ 97. Where the angular rotation is less than about 2 degrees, the angular rotation may be given by the following simplified relationship:

$$\Phi = \tfrac{1}{2} \arctan(x \div L) \quad \text{(eq. 5)}$$

The angular rotation given by equation 4 or equation 5 may be used in equation 1 to determine the torque developed in the bearings.

The operation of the invention is best understood by example. Initially, the bearings 11,12 to be tested are received in the test shaft apertures 30,31, and the pivots 64,65 are supported in the bearing cylindrical apertures 18 by the ball bearings 15. Because the pivots 64,65 are eccentric to the pendulum center of gravity, the pendulum 62 will have a tendency to "right" itself due to the effects of gravity, so that the pendulum center of gravity is directly below the axis of the pivots (axis) 105 (of FIG. 4) on a line perpendicular to the axis 105 and the earth. The laser 75 and the array 80 are aligned so that laser light is reflected off the panel 71 into approximately the center of the array 80.

The motor 60 is then operated, rotating the drive shaft 50 and drive pulleys 47,48, driving the test shaft pulleys 26,27 with the drive belts 45,46 to drive the test shafts 24,25 at approximately 0.5 revolutions per minute. As the test shafts 24,25 rotate, the bearing housings 5 and the outer race of the bearings 11,12 are rotated. The force of gravity will tend to maintain the pendulum 62 righted, while friction of the ball bearings will translate the rotational force of the outer race 17 to the gyroscope pivots 64,65, producing a rotational torque tending to displace the pendulum 62 from its righted position. As previously described, the displacement of the pendulum produces a change in the angle of incidence and angle of reflection of the laser beam, thereby producing a deflection of laser light on the array. The magnitude of the deflection is directly proportional to the angular rotation of the pendulum, and therefore directly proportional to the torque developed in the bearings during rotation.

In practice, complex conversions of displacement to torque are not required. Rather, the displacement measurement of bearing and pivot pairs is compared to the displacement measurement of bearing and pivot pairs known to be acceptable for use in a gyroscope. It has been found that this method of qualitative analysis provides an accurate method of determining the acceptability of bearing and pivot pairs for use in precision gyroscopes.

Although the invention is described as being used with a drive system employing pulleys and drive belts, other drive mechanisms would work equally as well, such as a combination of gears. In addition, although a laser and light sensitive array are used to sense rotation of the pendulum, other non-contacting sensing means, such as a mechanical position sensor, could be used without departing from the spirit and scope of the present invention.

Although the invention has been shown and described with respect to an exemplary embodiment thereof, it should be understood by those skilled in the art that various changes, omissions and additions may be made therein and thereto, without departing from the spirit and scope of the present invention.

We claim:

1. Apparatus for measuring torque generated between component parts in a pair of bearings, the torque being indicative of geometric and material defects of a component part in at least one bearing in the pair of bearings or contamination within at least one bearing in the pair of bearings, comprising:

a pair of axially aligned, rotatable test shafts, a first end of one of said test shafts facing a first end of another of said test shafts, each of said first ends having a cylindrical aperture of slightly larger diameter than an outside diameter of the bearings, the bearings being press fit into said apertures in axial alignment with one another, friction between the bearings and the test shafts being sufficient to prevent relative movement therebetween, whereby said bearings rotate in response to rotation of said test shafts;

means for rotating said test shafts;

a pendulum, having a pair of shafts extending outwardly on opposing sides of said pendulum, said shafts being in axial alignment with one another and being eccentric to the pendulum center of gravity, said pendulum being disposed between said bearing pair, said pendulum being supported by the bearings on said pendulum shafts; and measuring means for measuring any displacement of said pendulum when the bearings are rotated, said displacement being proportional to torque in the bearings.

2. Apparatus according to claim 1 wherein said pendulum further comprises:

a cylindrical aperture extending through the entire thickness of said pendulum, the aperture being eccentric to the pendulum center of gravity; and a pair of cylindrically shaped pivots, said pivots having an outside diameter slightly less than an inside diameter of said aperture, said pivots being press fit into said aperture on opposing sides of said pendulum, friction therebetween being sufficient to prevent relative movement.

3. Apparatus according to claim 1 wherein said means for rotating said test shafts comprises:

a motor having a rotatable motor shaft;

a rotatable drive shaft axially aligned with, and coupled to said motor shaft;

a pair of drive pulleys mounted to said drive shaft;

a pair of shaft pulleys mounted to a second end of said test shafts, said shaft pulleys being aligned with said drive pulleys; and a pair of drive belts, each drive belt coupling one of said drive pulleys to one of said shaft pulleys for rotating said test shafts in response to operating said motor.

4. Apparatus according to claim 1 wherein said measuring means comprises:

a laser light source;

detecting means for detecting laser light; and reflecting means affixed to said pendulum for reflecting laser light from said laser light source onto said detecting means at a first position on said detecting means, said position changing in response to displacement of said pendulum, said change in position being proportional to torque in the bearings.

5. Apparatus for measuring torque generated between component parts in a pair of high accuracy, close tolerance, precision output axis suspension bearings and corresponding pivots, comprising:

a pair of axially aligned, rotatable test shafts for holding each bearing in the pair of bearings in axial alignment with one another, a first end of one of said test shafts facing a first end of another of said test shafts, each of said first ends having a cylindrical aperture of slightly larger diameter than an outside diameter of the bearings, the bearings being press fit into said apertures, friction therebetween being sufficient to prevent relative movement;

means for rotating the bearing pair;

a pendulum having a cylindrical aperture extending through the entire thickness of the pendulum, the aperture being eccentric to the pendulum center of gravity and having an inside diameter slightly larger than the outside diameter of the pivots, the pivots being press fit into said aperture on opposing sides of said pendulum, friction therebetween being sufficient to prevent relative movement, said pendulum being disposed between said bearing pair in that said pivots are received in the bearings, said pendulum being supported by the bearings on the pivots; and measuring means for measuring any displacement of said pendulum when the bearings are rotated, said displacement being proportional to torque in the bearings.

6. Apparatus according to claim 5 wherein said means for rotating the bearing pair comprises:
   a motor having a rotatable motor shaft;
   a rotatable drive shaft axially aligned with, and coupled to said motor shaft;
   a pair of drive pulleys mounted to said drive shaft;
   a pair of shaft pulleys mounted to a second end of said test shafts, said shaft pulleys being aligned with said drive pulleys; and
   a pair of drive belts, each drive belt coupling one of said drive pulleys to one of said shaft pulleys for rotating said test shafts in response to operating said motor.

7. Apparatus according to claim 5 wherein said measuring means comprises:
   a laser light source;
   detecting means for detecting laser light; and
   reflecting means affixed to said pendulum for reflecting laser light from said laser light source onto said detecting means at a first position on said detecting means, said position changing in response to displacement of said pendulum, said change in position being proportional to torque in the bearings.

* * * * *